United States Patent
Jiang et al.

(10) Patent No.: US 11,312,963 B2
(45) Date of Patent: Apr. 26, 2022

(54) COMPOSITIONS AND METHODS FOR INHIBITING TIGIT GENE EXPRESSION

(71) Applicant: SynerK Inc., Concord, MA (US)

(72) Inventors: Weiwen Jiang, Winchester, MA (US); Jimmy X. Tang, Southborough, MA (US); Daqing Wang, North Reading, MA (US); Dong Yu, Westborough, MA (US)

(73) Assignee: SynerK Inc., Concord, MA (US)

( * ) Notice: Subject to any disclaimer, the term of this patent is extended or adjusted under 35 U.S.C. 154(b) by 5 days.

(21) Appl. No.: 16/655,484

(22) Filed: Oct. 17, 2019

(65) Prior Publication Data

US 2020/0149050 A1     May 14, 2020

Related U.S. Application Data

(60) Provisional application No. 62/747,261, filed on Oct. 18, 2018.

(51) Int. Cl.
| | |
|---|---|
| *C12N 15/113* | (2010.01) |
| *A61K 31/7125* | (2006.01) |
| *A61P 35/00* | (2006.01) |

(52) U.S. Cl.
CPC ...... *C12N 15/1138* (2013.01); *A61K 31/7125* (2013.01); *A61P 35/00* (2018.01); *C12N 2310/11* (2013.01); *C12N 2310/315* (2013.01)

(58) Field of Classification Search
CPC ...... A61P 35/00; A61P 37/00; A61K 31/7125; C12N 15/113; C12N 15/1138; C12N 2310/11; C12N 2310/315; C12N 2320/30; C12N 2320/31
USPC ............... 435/6.1, 91.1, 91.31, 455, 458; 514/44 A; 536/23.1, 23.5
See application file for complete search history.

(56) References Cited

U.S. PATENT DOCUMENTS

| | | | |
|---|---|---|---|
| 8,084,598 B1 * | 12/2011 | Bentwich ............... | G16B 20/30 536/24.5 |
| 2013/0095102 A1 | 4/2013 | Levin et al. | |
| 2017/0145412 A1 | 5/2017 | Jiang et al. | |
| 2019/0284529 A1 * | 9/2019 | Benson ............... | C07K 16/2803 |
| 2019/0309259 A1 * | 10/2019 | Meissner ............ | C12N 5/0696 |
| 2021/0102203 A1 * | 4/2021 | Krieg .................. | A61K 47/555 |
| 2021/0147569 A1 * | 5/2021 | Press ................... | A61P 35/00 |

FOREIGN PATENT DOCUMENTS

| | | | | |
|---|---|---|---|---|
| WO | WO-2019004939 A1 * | 1/2019 | ......... | C12N 15/1136 |
| WO | WO-2019094847 A1 * | 5/2019 | ............. | A61K 35/17 |

OTHER PUBLICATIONS

"*Homo sapiens* T cell immunoreceptor with Ig and ITIM domains (TIGIT) mRNA, complete cds", Publication [online], Jul. 8, 2009 [retrieved Jan. 24, 2020], Retrieved from the Internet: URL: https://www.ncbi.nlm.nih.gov/nuccore/EU675310>; pp. 1.
Chauvin, J.M. et al., "TIGIT and PD-1 impair tumor antigen-specific CD8+T cells in melanoma patients", J. Clin. Invest., vol. 125, No. 5, 2015, 2046-2058.
Chew, G. et al., "TIGIT Marks Exhausted T Cells, Correlates with Disease Progression, and Serves as a Target for Immune Restoration in HIV and SIV Infection", PLoS Pathogens, e1005349, 2016, 1-28.
Guillerey, C. et al., "TIGIT immune checkpoint blockade restores CD8+ T-cell immunity against multiple myeloma", Blood, vol. 132, No. 16, 2018, 1689-1694.
Pauken, K. et al., "TIGIT and CD226: Tipping the Balance between Costimulatory and Coinhibitory Molecules to Augment the Cancer Immunotherapy Toolkit", Cancer Cell, vol. 26, 2014, 785-787.
Stanietsky, N. et al., "The interaction of TIGIT with PVR and PVRL2 inhibits human NK cell cytotoxicity", PNAS, vol. 106, No. 42, 2009, 17858-17863.
Yu, X. et al., "The surface protein TIGIT suppresses T cell activation by promoting the generation of mature immunoregulatory dendritic cells", Nature Immunology, vol. 10, No. 1, 2009, 48-57.

* cited by examiner

*Primary Examiner* — Jane J Zara
(74) *Attorney, Agent, or Firm* — Elmore Patent Law Group, P.C.; Joseph C. Zucchero; Carolyn S. Elmore

(57) ABSTRACT

Disclosed herein are compounds, compositions, and methods for decreasing TIGIT mRNA and protein expression. Such methods are useful to treat, prevent, or ameliorate TIGIT associated diseases, disorders, and conditions.

4 Claims, 6 Drawing Sheets

Specification includes a Sequence Listing.

COMPOSITIONS AND METHODS FOR INHIBITING TIGIT GENE EXPRESSION

RELATED APPLICATION

This application claims the benefit of U.S. Provisional Application No. 62/747,261, filed on Oct. 18, 2018. The entire teachings of the above application are incorporated herein by reference.

BACKGROUND OF THE INVENTION

T cell immunoreceptor with Ig and ITIM domains (TIGIT, also known as VSIG9, WUCAM and VSTM3) is an immune checkpoint receptor known to negatively regulate T cell functions[1]. TIGIT is expressed on some T cells and natural killer (NK) cells[1] and it binds to poliovirus receptor (PVR/CD155) on dendritic cells and macrophages[1].

Interaction of TIGIT and PVR has been shown to negatively regulate T cell and NK cell functions[1]. Blocking the interaction of TIGIT and PVR/CD155 can reverse its inhibitory effect on NK cell cytotoxicity[2]. In HIV patients, TIGIT expression has been correlated with disease progression due to its ability to cause T cell exhaustion[3]. Blocking TIGIT along with PD-1 (programmed death protein-1) with monoclonal antibodies can rescue HIV specific CD8+ T cell responses[3].

TIGIT expression is highly correlated with other immune checkpoints such as PD-1 on TILs. This expression pattern is directly linked to an immunosuppressive phenotype. In preclinical settings, TIGIT knockout mice showed reduced tumor burden and prolonged survival in murine models[4]. Moreover, simultaneous blocking TIGIT and PD-1 in melanoma patients resulted in tumor antigen specific CD8+ T cell proliferation and CD8+ tumor infiltrating T cells (TILs)[5].

In addition, TIGIT can also compete with CD226, a T cell co-stimulatory molecule for its binding to CD155[6]. Data also suggest that TIGIT can impede the dimerization of CD226 abolishing its co-stimulatory activity[6]. Taken together, inhibiting TIGIT can provide a therapeutic benefit to rejuvenate T cell activity in disease settings such as cancer, viral infection and in inflammatory diseases/conditions.

SUMMARY OF THE INVENTION

Certain embodiments provide antisense compounds, compositions and methods for use in therapy. In certain embodiments, the compositions and methods for therapy include administering a T cell immunoreceptor with Ig and ITIM domains (TIGIT; also known as VSIG9, WUCAM and VSTM3) specific inhibitor to an individual in need thereof. In certain embodiments, the TIGIT specific inhibitor is a nucleic acid. In certain embodiments, the nucleic acid is an antisense compound targeting TIGIT as described herein. Certain embodiments the compounds, compositions and methods are useful for preventing, treating, delaying, slowing the progression and/or ameliorating TIGIT related diseases, disorders, and conditions. In certain embodiments, such diseases, disorders, and conditions are cancer, inflammatory diseases such as but not limited to systemic lupus erythematosus, systemic sclerosis, ulcerative colitis, multiple sclerosis, rheumatoid arthritis, Crohn's disease, nonalcoholic steatohepatitis and sepsis, viral infections such as HIV, hepatitis B or hepatitis C.

Provided herein are compounds, compositions and methods for inhibiting expression of TIGIT mRNA and/or protein. Also provided herein are methods for diagnosing, treating and/or preventing diseases and/or conditions that respond to the inhibiting expression of TIGIT mRNA and/or protein.

In certain embodiments, the TIGIT specific inhibitor is a synthetic oligonucleotide compound comprising 12 to 30 linked nucleotides having at least 12 contiguous nucleobases complementary to an equal length portion of SEQ ID NO: 1. In certain embodiments, the internucleotide linkages of the compound comprise phosphorothioate internucletide linkages. In some embodiments more than half but less that all of the internucleotide linkages are phosphorothioate internucleotide linkages. In some embodiments all of the internucleotide linkages are phosphorothioate internucleotide linkages. In certain embodiments, the phosphorothioate linkages may be mixed Rp and Sp enantiomers, or they may be made stereoregular or substantially stereoregular in either Rp or Sp form.

In certain embodiments, the compound is not further modified at its nucleobases (i.e., no base or sugar moiety modification). In this respect, the nucleotides of the antisense oligonucleotide comprise naturally occurring nucleobases and sugars.

In certain embodiments, the TIGIT specific inhibitor is a synthetic oligonucleotide compound comprising 12 to 30 linked nucleotides wherein the nucleobase sequence of the compound is at least 80% complementary to an equal length portion of SEQ ID NO: 1. In certain embodiments, the internucleotide linkages of the compound comprise phosphorothioate internucletide linkages. In some embodiments more than half but less that all of the internucleotide linkages are phosphorothioate internucleotide linkages. In some embodiments all of the internucleotide linkages are phosphorothioate internucleotide linkages. In certain embodiments, the phosphorothioate linkages may be mixed Rp and Sp enantiomers, or they may be made stereoregular or substantially stereoregular in either Rp or Sp form. In certain embodiments, the compound is not further modified at its nucleobases (i.e., no base or sugar moiety modification). In this respect, the nucleotides of the antisense oligonucleotide comprise naturally occurring nucleobases and sugars.

In certain embodiments, the TIGIT specific inhibitor is a synthetic oligonucleotide compound comprising 12 to 30 linked nucleotides wherein the nucleobase sequence of the compound is at least 80% complementary to an equal length portion of nucleobases 121-780, 841-1440, 1650-2160, or 2700-2800 of SEQ ID NO: 1. In certain embodiments, the internucleotide linkages of the compound comprise phosphorothioate internucletide linkages. In some embodiments more than half but less that all of the internucleotide linkages are phosphorothioate internucleotide linkages. In some embodiments all of the internucleotide linkages are phosphorothioate internucleotide linkages. In certain embodiments, the phosphorothioate linkages may be mixed Rp and Sp enantiomers, or they may be made stereoregular or substantially stereoregular in either Rp or Sp form. In certain embodiments, the compound is not further modified at its nucleobases (i.e., no base or sugar moiety modification). In this respect, the nucleotides of the antisense oligonucleotide comprise naturally occurring nucleobases and sugars.

Certain embodiments provide a composition comprising a compound described herein, and a pharmaceutically acceptable carrier or diluent.

In some embodiments, the invention provides a method for inhibiting TIGIT mRNA or protein expression. In some embodiments, the method comprises contacting a cell with at least one antisense compound composition as described herein. In some embodiments, the method comprises administering at least one antisense compound or composition as described herein.

In certain embodiments, the inhibition of TIGIT expression occurs in a cell or tissue. In certain embodiments, the inhibition occurs in a cell or tissue in an animal. In certain embodiments, the animal is a human. In certain embodiments, the inhibition is a reduction in TIGIT mRNA level. In certain embodiments, the inhibition is a reduction in TIGIT protein level. In certain embodiments, both TIGIT mRNA and protein levels are reduced.

In some embodiments, the invention provides a method for treating a disease, disorder, or condition associated with TIGIT expression and/or activity in an individual in need thereof. In some embodiments, the method comprises administering at least one antisense compound or composition as described herein.

DETAILED DESCRIPTION

Figure 1:
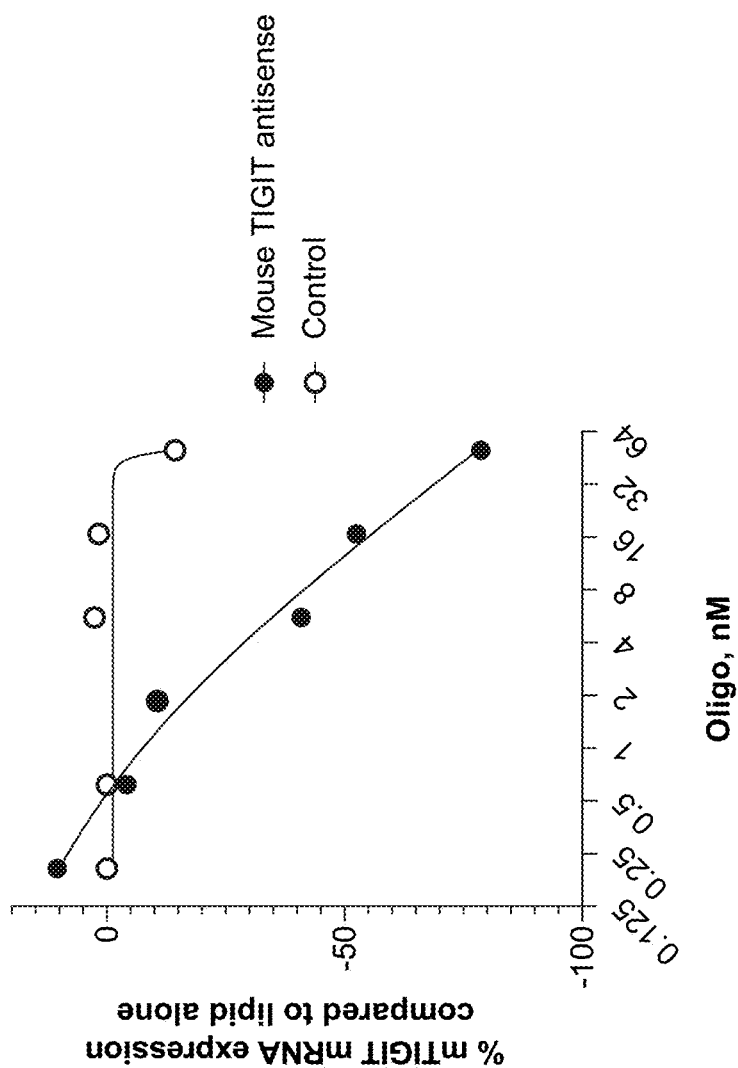
FIG. 1 depicts the effects of a TIGIT antisense analog in mouse CT26.CL25 cell line.

It is to be understood that both the foregoing general description and the following detailed description are exemplary and explanatory only and are not restrictive of the disclosure. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting.

Any section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

Unless specific definitions are provided, the nomenclature used in connection with, and the procedures and techniques of, analytical chemistry, synthetic organic chemistry, and medicinal and pharmaceutical chemistry described herein are those well-known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21.sup.st edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," 2.sup.nd Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

The term "3'", when used directionally, generally refers to a region or position in a polynucleotide or oligonucleotide 3' (toward the 3'end of the nucleotide) from another region or position in the same polynucleotide or oligonucleotide. The term "3' end" generally refers to the 3' terminal nucleotide of the component oligonucleotides.

The term "5'", when used directionally, generally refers to a region or position in a polynucleotide or oligonucleotide 5' (toward the 5'end of the nucleotide) from another region or position in the same polynucleotide or oligonucleotide. The term "5' end" generally refers to the 5' terminal nucleotide of the component oligonucleotides.

As used herein, "chemical modification" means a chemical difference in a compound when compared to a naturally occurring counterpart. Chemical modifications of oligonucleotides include nucleoside modifications, including sugar moiety modifications and nucleobase modifications, and internucleoside linkage modifications. In reference to an oligonucleotide, chemical modification does not include differences only in nucleobase sequence.

As used herein, "sugar moiety" means a naturally occurring sugar moiety or a modified sugar moiety of a nucleoside. As used herein, "naturally occurring sugar moiety" means a ribofuranosyl as found in naturally occurring RNA or a deoxyribofuranosyl as found in naturally occurring DNA. As used herein, "modified sugar moiety" means a substituted sugar moiety or a sugar surrogate.

As used herein, "nucleic acid" refers to molecules composed of monomeric nucleotides. A nucleic acid includes ribonucleic acids (RNA), deoxyribonucleic acids (DNA), single-stranded nucleic acids (ssDNA), double-stranded nucleic acids (dsDNA), small interfering ribonucleic acids (siRNA), and microRNAs (miRNA).

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified. As used herein, "nucleobase sequence" means the order of contiguous nucleobases independent of any sugar, linkage, or nucleobase modification.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA). In certain embodiments, an oligonucleotide comprises only unmodified ribonucleosides (RNA) and/or unmodified deoxyribonucleosides (DNA). In certain embodiments, an oligonucleotide comprises one or more modified nucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide. As used herein "naturally occurring internucleoside linkage" means a 3' to 5' phosphodiester linkage. As used herein, "modified internucleoside linkage" means any internucleoside linkage other than a naturally occurring internucleoside linkage.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid. In certain embodiments, antisense activity includes modulation of the amount or activity of a target nucleic acid transcript (e.g. mRNA). In certain embodiments, antisense activity includes modulation of the splicing of pre-mRNA.

As used herein, "RNase H based antisense compound" means an antisense compound wherein at least some of the antisense activity of the antisense compound is attributable to hybridization of the antisense compound to a target nucleic acid and subsequent cleavage of the target nucleic acid by RNase H.

As used herein, "RISC based antisense compound" means an antisense compound wherein at least some of the antisense activity of the antisense compound is attributable to the RNA Induced Silencing Complex (RISC).

As used herein, "expression" means the process by which a gene ultimately results in a protein. Expression includes, but is not limited to, transcription, post-transcriptional modification (e.g., splicing, polyadenylation, addition of 5'-cap), and translation.

As used herein, "target nucleic acid" means a nucleic acid molecule to which an antisense compound is intended to hybridize to result in a desired antisense activity. Antisense oligonucleotides have sufficient complementarity to their target nucleic acids to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compound are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

The term "linear synthesis" generally refers to a synthesis that starts at one end of an oligonucleotide and progresses linearly to the other end. Linear synthesis permits incorporation of either identical or non-identical (in terms of length, base composition and/or chemical modifications incorporated) monomeric units into an oligonucleotide.

As used herein, "About" means within +/−10% of a value. For example, if it is stated, "a marker may be increased by about 50%", it is implied that the marker may be increased between 45%-55%.

As used herein, "administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

As used herein, "administering" or "administration" means providing a pharmaceutical agent to an individual, and includes, but is not limited to, administering by a medical professional and self-administering. Administration of a pharmaceutical agent to an individual can be continuous, chronic, short or intermittent. Administration can parenteral or non-parenteral.

As used herein, "agent" means an active substance that can provide a therapeutic benefit when administered to an animal. "First agent" means a therapeutic compound of the invention. For example, a first agent can be an antisense oligonucleotide targeting TIGIT. "Second agent" means a second therapeutic compound of the invention (e.g. a second antisense oligonucleotide targeting TIGIT) and/or a non-TIGIT therapeutic compound.

As used herein, "effective amount" or "therapeutically effective amount" means the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

As used herein, "individual" or "subject" or "animal" means a human or non-human animal selected for treatment or therapy. As used herein, "individual in need thereof" refers to a human or non-human animal selected for treatment or therapy that is in need of such treatment or therapy.

As used herein, "inhibiting the expression or activity" refers to a reduction or blockade of the expression or activity of a RNA or protein and does not necessarily indicate a total elimination of expression or activity.

As used herein, "pharmaceutical agent" means a substance that provides a therapeutic benefit when administered to an individual. For example, in certain embodiments, an antisense oligonucleotide targeted to TIGIT is a pharmaceutical agent. As used herein, "pharmaceutical composition" or "composition" means a mixture of substances suitable for administering to an individual. For example, a pharmaceutical composition can comprise one or more active agents and a pharmaceutical carrier e.g., a sterile aqueous solution.

As used herein, "region" or "target region" is defined as a portion of the target nucleic acid having at least one identifiable structure, function, or characteristic. For example, a target region may encompass a 3' UTR, a 5' UTR, an exon, an intron, an exon/intron junction, a coding region, a translation initiation region, translation termination region, or other defined nucleic acid region. The structurally defined regions for TIGIT can be obtained by accession number from sequence databases such as NCBI and such information is incorporated herein by reference. In certain embodiments, a target region may encompass the sequence from a 5' target site of one target segment within the target region to a 3' target site of another target segment within the target region.

As used herein, "treat", "treatment", or "treating" refers to administering a compound described herein to effect an alteration or improvement of a disease, disorder, or condition.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

Certain embodiments provide compounds and methods for decreasing TIGIT mRNA and protein expression. In certain embodiments, the compound is a TIGIT specific inhibitor for treating, preventing, or ameliorating a TIGIT associated disease. In certain embodiments, the compound is an antisense oligonucleotide targeting TIGIT.

In certain embodiments provided are antisense compounds targeted to a human TIGIT nucleic acid. In certain embodiments, the human TIGIT nucleic acid is the sequence set forth in GENBANK Accession No. NM_173799.3 (incorporated herein as SEQ ID NO: 1).

(SEQ ID NO: 1)

```
  1 cgtcctatct gcagtcggct actttcagtg gcagaagagg ccacatctgc ttcctgtagg
 61 ccctctgggc agaagcatgc gctggtgtct cctcctgatc tgggcccagg ggctgaggca
121 ggctccccct gcctcaggaa tgatgacagg cacaatagaa acaacgggga acatttctgc
181 agagaaaggt ggctctatca tcttacaatg tcacctctcc tccaccacgg cacaagtgac
241 ccaggtcaac tgggagcagc aggaccagct tctggccatt tgtaatgctg acttggggtg
301 gcacatctcc ccatccttca aggatcgagt ggccccaggt cccggcctgg gcctcaccct
```

-continued

```
 361 ccagtcgctg accgtgaacg atacagggga gtacttctgc atctatcaca cctaccctga
 421 tgggacgtac actgggagaa tcttcctgga ggtcctagaa agctcagtgg ctgagcacgg
 481 tgccaggttc cagattccat tgcttggagc catggccgcg acgctggtgg tcatctgcac
 541 agcagtcatc gtggtggtcg cgttgactag aaagaagaaa gccctcagaa tccattctgt
 601 ggaaggtgac ctcaggagaa atcagctgg acaggaggaa tggagcccca gtgctccctc
 661 accccagga agctgtgtcc aggcagaagc tgcacctgct gggctctgtg agagcagcg
 721 gggagaggac tgtgccgagc tgcatgacta cttcaatgtc ctgagttaca aagcctggg
 781 taactgcagc ttcttcacag agactggtta gcaaccagag gcatcttctg gaagatacac
 841 ttttgtcttt gctattatag atgaatatat aagcagctgt actctccatc agtgctgcgt
 901 gtgtgtgtgt gtgtgtatgt gtgtgtgtgt tcagttgagt gaataaatgt catcctcttc
 961 tccatcttca tttccttggc cttttcgttc tattccattt tgcattatgg caggcctagg
1021 gtgagtaacg tggatcttga tcataaatgc aaaattaaaa aatatcttga cctggtttta
1081 aatctggcag tttgagcaga tcctatgtct ctgagagaca cattcctcat aatggccagc
1141 attttgggct acaaggtttt gtggttgatg atgaggatgg catgactgca gagccatcct
1201 catctcattt tttcacgtca ttttcagtaa cttttcactca ttcaaaggca ggttataagt
1261 aagtcctggt agcagcctct atggggagat ttgagagtga ctaaatcttg gtatctgccc
1321 tcaagaactt acagttaaat ggggagacaa tgttgtcatg aaaaggtatt atagtaagga
1381 gagaaggaga catacacagg ccttcaggaa gagacgacag tttggggtga ggtagttggc
1441 ataggcttat ctgtgatgaa gtggcctggg agcaccaagg ggatgttgag gctagtctgg
1501 gaggagcagg agttttgtct agggaacttg taggaaattc ttggagctga aagtcccaca
1561 aagaaggccc tggcaccaag ggagtcagca aacttcagat tttattctct gggcaggcat
1621 ttcaagtttc cttttgctgt gacatactca tccattagac agcctgatac aggcctgtag
1681 cctcttccgg ccgtgtgtgc tggggaagcc ccaggaaacg cacatgccca cacagggagc
1741 caagtcgtag catttgggcc ttgatctacc ttttctgcat caatacactc ttgagccttt
1801 gaaaaaagaa cgtttcccac taaaaagaaa atgtggattt ttaaaatagg gactcttcct
1861 aggggaaaaa gggggggctgg gagtgataga gggtttaaaa aataaacacc ttcaaactaa
1921 cttcttcgaa cccttttatt cactccctga cgactttgtg ctgggggttgg ggtaactgaa
1981 ccgcttattt ctgtttaatt gcattcaggc tggatcttag aagacttttta tccttccacc
2041 atctctctca gaggaatgag cggggaggtt ggatttactg gtgactgatt ttctttcatg
2101 ggccaaggaa ctgaaagaga atgtgaagca aggttgtgtc ttgcgcatgg ttaaaaataa
2161 agcattgtcc tgcttcctaa gacttagact ggggttgaca attgttttag caacaagaca
2221 attcaactat ttctcctagg attttttatta ttattatttt ttcacttttc taccaaatgg
2281 gttacatagg aagaatgaac tgaaatctgt ccagagctcc aagtcctttg gaagaaagat
2341 tagatgaacg taaaaatgtt gttgtttgct gtggcagttt acagcatttt tcttgcaaaa
2401 ttagtgcaaa tctgttggaa atagaacaca attcacaaat tggaagtgaa ctaaaatgta
2461 atgacgaaaa gggagtagtg ttttgatttg gaggaggtgt atattcggca gaggttggac
2521 tgagagttgg gtgttatta acataattat ggtaattggg aaacatttat aaacactatt
2581 gggatggtga taaaatacaa aagggcctat agatgttaga aatgggtcag gttactgaaa
2641 tgggattcaa tttgaaaaaa attttttaa atagaactca ctgaactaga ttctcctctg
2701 agaaccagag aagaccattt catagttgga ttcctggaga catgcgctat ccaccacgta
2761 gccactttcc acatgtggcc atcaaccact taagatgggg ttagtttaaa tcaagatgtg
```

-continued

```
2821 ctgttataat tggtataagc ataaaatcac actagattct ggagatttaa tatgaataat 2881 aagaatacta tttcagtagt tttggtatat tgtgtgtcaa aaatgataat attttggatg 2941 tattgggtga aataaaatat taacattaaa aaaaaaaa
```

In certain embodiments provided are antisense compounds targeted to a mouse TIGIT nucleic acid. In certain embodiments, the mouse TIGIT nucleic acid is the sequence set forth in GENBANK Accession No. EU675311.1 (incorporated herein as SEQ ID NO: 52).

(SEQ ID NO: 52)
```
  1 gccagtttca gttggaggag aggccacatc cactttgctg taggcctctg gttagaagca 61 tgcatggctg gctgctcctg gtctgggtcc aggggctgat acaggctgcc ttcctcgcta 121 caggagccac agcaggcacg atagatacaa agaggaacat ctctgcagag gaaggtggct 181 ctgtcatctt acagtgtcac ttctcctctg acacagctga agtgacccaa gtcgactgga 241 agcagcagga ccagcttctg gccatttata gtgttgacct ggggtggcat gtcgcttcag 301 tcttcagtga tcgggtggtc ccaggcccca gcctaggcct caccttccag tctctgacaa 361 tgaatgacac gggagagtac ttctgtacct atcatacgta tcctggtggg atttacaagg 421 ggagaatatt cctgaaggtc caagaaagct cagtggctca gttccagact gccccgcttg 481 gaggaaccat ggctgctgtg ctgggactca tttgcttaat ggtcacagga gtgactgtac 541 tggctagaaa gaagtctatt agaatgcatt ctatagaaag tggccttggg agaacagaag 601 cggagccaca ggaatggaac ctgaggagtc tctcatcccc tggaagccct gtccagacac 661 aaactgcccc tgctggtccc tgtggagagc aggcagaaga tgactatgct gacccacagg 721 aatactttaa tgtcctgagc tacagaagcc tagagagctt cattgctgta tcgaagactg 781 gctaacgaca gctctctatc cctctcccta tgtctctctc tctgtctctc tctgtctctc 841 tctgtctctg tctctgtctc tgtctctctc tctctctctc tctctctctc tgtgtgtgtg 901 tgtgtgtatg tgtgtataca tcattaatgt tcattaacac taactgcata tggtggagga 961 ccaggaaata aaagtttgtg ttgctaataa aattaagtgc taactt
```

Certain embodiments provide a compound targeting TIGIT, wherein the compound comprises of 12 to 30 linked nucleosides. In certain embodiments, the compound consists of 15 to 30, 18 to 24, 19 to 22, 13 to 25, 14 to 25, or 15 to 25 linked nucleosides. In certain embodiments, the compound comprises at least 12, at least 13, at least 14, at least 15, at least 16, at least 17, at least 18, at least 19, at least 20, at least 21, at least 22, at least 23, at least 24, at least 25, at least 26, at least 27, at least 28, at least 29 or 30 linked nucleosides. In certain embodiments, the compound consists of 20 linked nucleosides. In certain embodiments, the compound consists of 22 linked nucleosides.

Certain embodiments provide a compound targeting TIGIT, wherein the compound consists of 12 to 30 linked nucleosides and has a nucleobase sequence comprising at least 8, at least 9, at least 10, at least 11, at least 12, at least 13, at least 14, at least 15, at least 16, at least 17, at least 18, at least 19, at least 20, at least 21, or 22 contiguous nucleobases of any of the nucleobase sequences of SEQ ID NO: 1. In certain embodiments, the compound has a nucleobase sequence comprising at least 12 contiguous nucleobases of any one of the nucleobase sequences of SEQ ID NO: 1.

Certain embodiments provide a compound targeting TIGIT, wherein the compound comprises at least 8, at least 9, at least 10, at least 11, at least 12, at least 13, at least 14, at least 15, at least 16, at least 17, at least 18, at least 19, at least 20, at least 21, or 22 contiguous nucleobases complementary to an equal length portion of any of SEQ ID NOs: 1 or 27-51.

Certain embodiments provide a compound targeting a TIGIT segment, wherein the compound comprises at least 8, at least 9, at least 10, at least 11, at least 12, at least 13, at least 14, at least 15, at least 16, at least 17, at least 18, at least 19, at least 20, at least 21, or 22 contiguous nucleobases complementary to an equal length portion of any of the target segments shown in, for example, Table 1. In the table, the "Start Site" refers to the 5'-most nucleotide of a target segment and "Stop Site" refers to the 3'-most nucleotide of a target segment. A target segment can range from the start site to the stop site of each sequence listed in the table. Alternatively, the target segment can range from the start site of one sequence and end at the stop site of another sequence. For example, as shown in Table 1, a target segment can range from 151-172, the start site to the stop site of SEQ ID NO: 27. In another example, as shown in Table 1, a target segment can range from 319-440, the start site of SEQ ID NO: 29 to the stop site of SEQ ID NO: 32.

Certain embodiments provide a compound targeting TIGIT, wherein the nucleobase sequence of the compound is at least 80%, at least 85%, at least 90%, at least 95%, or 100% complementary to SEQ ID NO: 1. Certain embodiments provide a compound targeting TIGIT, wherein the nucleobase sequence of the compound is at least 80%, at least 85%, at least 90%, at least 95%, or 100% complementary to any of the target segments shown in, for example, Table 1.

In certain embodiments, the gene silencing compound targets anywhere within the region spanning from nucleobase 121-300, 301-600, 601-780, 900-1250, 1251-1440, or 1920-2400 of SEQ ID NO: 1.

In certain embodiments, the gene silencing compound targets anywhere within the region spanning from nucleobase 100 to 300, 150 to 250, 175 to 225, 180-220, 50 to 250, 100 to 250, 150 to 350, 150 to 300, 300 to 500, 350 to 450, 375 to 425, 385-425, 250 to 450, 300 to 450, 300 to 550, 350 to 550, or 350 to 500, 300 to 800, 500 to 800, 550 to 750, 800 to 1150, 900 to 1250, 1150 to 1400, 1200 to 1350, 1225 to 1325, 1240-1300, 1050 to 1350, 1100 to 1350, 1200 to 1450, 1200 to 1400, 1400 to 1700, 1650 to 1800, 1650 to 2160, 1650 to 2200, 1600 to 1900, 1900 to 2200, 1900 to 2400, 2160 to 2500, 2300 to 2600, 2700 to 2800, or 2500 to 2978 of SEQ ID NO: 1.

In certain embodiments, the gene silencing compound targets anywhere within the region spanning from nucleobase 100 to 300, 150 to 250, 175 to 225, 180-220, 50 to 250, 100 to 250, 150 to 350, or 150 to 300 of SEQ ID NO: 1.

In certain embodiments, the gene silencing compound targets anywhere within the region spanning from nucleobase 300 to 500, 350 to 450, 375 to 425, 385-425, 250 to 450, 300 to 450, 300 to 550, 350 to 550, or 350 to 500, 300 to 800, 500 to 800, 550 to 750, 800 to 1150, 900 to 1250 of SEQ ID NO: 1.

In certain embodiments, the gene silencing compound targets anywhere within the region spanning from nucleobase 1150 to 1400, 1200 to 1350, 1225 to 1325, 1240-1300, 1050 to 1350, 1100 to 1350, 1200 to 1450, 1200 to 1400 of SEQ ID NO: 1.

In certain embodiments, the gene silencing compound targets anywhere within the region spanning from nucleobase 1400 to 1700, 1650 to 1800, 1650 to 2160, 1650 to 2200, 1600 to 1900, 1900 to 2200, 1900 to 2400, 2160 to 2500, 2300 to 2600, 2700 to 2800, or 2500 to 2978 of SEQ ID NO: 1.

In certain embodiments, the gene silencing compound targets anywhere within the region spanning from nucleobase 300 to 800 of SEQ ID NO: 1.

In certain embodiments, the gene silencing compound targets anywhere within the region spanning from nucleobase 300 to 450 of SEQ ID NO: 1.

In certain embodiments, the gene silencing compound targets anywhere within the region spanning from nucleobase 300 to 550 of SEQ ID NO: 1.

In certain embodiments, the gene silencing compound targets anywhere within the region spanning from nucleobase 900 to 1250 of SEQ ID NO: 1.

In certain embodiments, the gene silencing compound targets anywhere within the region spanning from nucleobase 1600 to 1900 of SEQ ID NO: 1.

In certain embodiments, the gene silencing compound targets anywhere within the region spanning from nucleobase 1650 to 2200 of SEQ ID NO: 1.

In certain embodiments, the gene silencing compound targets anywhere within the region spanning from nucleobase 1650 to 2160 of SEQ ID NO: 1.

In certain embodiments, the gene silencing compound targets anywhere within the region spanning from nucleobase 1900 to 2200 of SEQ ID NO: 1.

Also included within these embodiments are gene silencing compounds that target regions of SEQ ID NO: 1 within the regions specified, i.e. sub-regions within the specified regions.

Certain embodiments provide a compound targeting TIGIT, wherein the compound consists of 12 to 30 linked nucleosides and has a nucleobase sequence comprising at least 8, at least 9, at least 10, at least 11, at least 12, at least 13, at least 14, at least 15, at least 16, at least 17, at least 18, at least 19, at least 20, at least 21, or 22 contiguous nucleobases of any of the nucleobase sequences of SEQ ID NOs: 2-26. In certain embodiments, the compound has a nucleobase sequence comprising at least 12 contiguous nucleobases of any one of the nucleobase sequences of SEQ ID NOs: 2-26. In certain embodiments, the compound consists of any one of SEQ ID NOs: 2-26.

Certain embodiments provide an antisense compound targeting TIGIT as described herein, wherein the compound is single-stranded.

Certain embodiments provide an antisense compound targeting TIGIT as described herein, wherein the oligonucleotide is unmodified.

Certain embodiments provide an antisense oligonucleotide targeting TIGIT as described herein, wherein the oligonucleotide comprises at least one modified internucleoside linkage. In certain embodiments, the modified internucleoside linkage is a phosphorothioate internucleoside linkage. In certain embodiments, at least 1, at least 2, at least 3, at least 4, at least 5, at least 6, at least 7, at least 8, at least 9 or at least 10 internucleoside linkages of said modified oligonucleotide are phosphorothioate internucleoside linkages. In some embodiments, the modified internucleotide linkage is a phosphorothioate internucleotide linkage. In some embodiments more than half but less that all of the internucleotide linkages are phosphorothioate internucleotide linkages. In some embodiments all of the internucleotide linkages are phosphorothioat internucleotide linkages. In certain embodiments, the phosphorothioate linkages may be mixed Rp and Sp enantiomers, or they may be made stereoregular or substantially stereoregular in either Rp or Sp form.

Certain embodiments provide an antisense oligonucleotide targeting TIGIT as described herein, wherein the oligonucleotide comprises at least one modified internucleotide linkage and wherein the nucleotides of the oligonucleotide comprise naturally occurring nucleobases and sugars.

Certain embodiments provide an antisense oligonucleotide targeting TIGIT as described herein, wherein the oligonucleotide comprises at least one modified internucleotide linkage and wherein at least one nucleotide of the oligonucleotide comprises a modified nucleobase, a modified sugar, or a combination thereof.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine. Further modified nucleobases include tricyclic pyrimidines such as phenoxazine cytidine ([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. In certain embodiments, the modified nucleobase is a 5-methylcytosine.

In certain embodiments, the modified sugar is a bicyclic sugar. In certain embodiments, the modified sugar comprises a 2'-O-methoxyethyl, a constrained ethyl, a 3'-fluoro-HNA or a 4'-(CH$_2$)$_n$—O-2' bridge, wherein n is 1 or 2.

Certain embodiments provide a compound comprising a modified oligonucleotide targeting TIGIT, wherein the modified oligonucleotide consists of 12 to 30 linked nucleosides and comprises: (a) a gap segment consisting of linked deoxynucleosides; (b) a 5' wing segment consisting of linked nucleosides; (c) a 3' wing segment consisting of linked nucleosides; and wherein the gap segment is positioned between the 5' wing segment and the 3' wing segment and wherein each nucleoside of each wing segment comprises a modified sugar.

Certain embodiments provide a compound comprising a modified oligonucleotide targeting TIGIT, wherein the modified oligonucleotide consists of 22 linked nucleosides and comprises: (a) a gap segment consisting of twelve linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein at least one internucleoside linkage is a phosphorothioate linkage and wherein each cytosine residue is a 5-methylcytosine.

Certain embodiments provide a compound comprising a modified oligonucleotide targeting TIGIT, wherein the modified oligonucleotide consists of 22 linked nucleosides and has a nucleobase sequence comprising at least 8 contiguous nucleobases of any of SEQ ID NOs: 2-26, wherein the modified oligonucleotide comprises: (a) a gap segment consisting of twelve linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein at least one internucleoside linkage is a phosphorothioate linkage and wherein each cytosine residue is a 5-methylcytosine.

In certain embodiments, a target nucleic acid is an RNA. In certain embodiments, a target nucleic acid is a non-coding RNA. In certain embodiments, a target nucleic acid encodes a protein. In certain embodiments, a target nucleic acid is selected from a mRNA, a pre-mRNA, a microRNA, a non-coding RNA, including small non-coding RNA, and a promoter-directed RNA.

In certain embodiments, the invention provides antisense oligonucleotides having a sequence complementary to a target nucleic acid. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid or reduce non-specific hybridization to non-target nucleic acid sequences under conditions in which specific hybridization is desired (e.g., under physiological conditions for in vivo or therapeutic uses, and under conditions in which assays are performed in the case of in vitro assays). In certain embodiments, oligonucleotides are selective between a target and non-target, even though both target and non-target comprise the target sequence. In such embodiments, selectivity may result from relative accessibility of the target region of one nucleic acid molecule compared to the other.

In certain embodiments, the present disclosure provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

In certain embodiments, oligonucleotides comprise a hybridizing region and a terminal region. In certain such embodiments, the hybridizing region consists of 12-30 linked nucleosides and is fully complementary to the target nucleic acid. In certain embodiments, the hybridizing region includes one mismatch relative to the target nucleic acid. In certain embodiments, the hybridizing region includes two mismatches relative to the target nucleic acid. In certain embodiments, the hybridizing region includes three mismatches relative to the target nucleic acid. In certain embodiments, the terminal region consists of 1-4 terminal nucleosides. In certain embodiments, the terminal nucleosides are at the 3' end. In certain embodiments, one or more of the terminal nucleosides are not complementary to the target nucleic acid.

Antisense mechanisms include any mechanism involving the hybridization of an oligonucleotide with target nucleic acid, wherein the hybridization results in a biological effect. In certain embodiments, such hybridization results in either target nucleic acid degradation or occupancy with concomitant inhibition or stimulation of the cellular machinery involving, for example, translation, transcription, or splicing of the target nucleic acid.

One type of antisense mechanism involving degradation of target RNA is RNase H mediated antisense. RNase H is a cellular endonuclease which cleaves the RNA strand of an RNA:DNA duplex. It is known in the art that single-stranded antisense compounds which are "DNA-like" elicit RNase H activity in mammalian cells. Activation of RNase H, therefore, results in cleavage of the RNA target, thereby greatly enhancing the efficiency of DNA-like oligonucleotide-mediated inhibition of gene expression.

The synthetic antisense compounds of the invention can be prepared by the art recognized methods such as phosphoramidate or H-phosphonate chemistry which can be carried out manually or by an automated synthesizer. The synthetic antisense compounds of the invention may also be modified in a number of ways without compromising their ability to hybridize to mRNA.

In some embodiments, the oligonucleotide-based compounds of the invention are synthesized by a linear synthesis approach.

An alternative mode of synthesis is "parallel synthesis", in which synthesis proceeds outward from a central linker moiety. A solid support attached linker can be used for parallel synthesis, as is described in U.S. Pat. No. 5,912,332. Alternatively, a universal solid support (such as phosphate attached controlled pore glass) support can be used.

At the end of the synthesis by either linear synthesis or parallel synthesis protocols, the oligonucleotide-based compounds of the invention may conveniently be deprotected with concentrated ammonia solution or as recommended by the phosphoramidite supplier, if a modified nucleoside is incorporated. The product oligonucleotide-based compounds is preferably purified by reversed phase HPLC, detritylated, desalted and dialyzed.

In certain embodiments, the oligonucleotides of the antisense compounds according to the invention are selected from the non-limiting list of the oligonucleotides shown in Table 1. Unless otherwise noted the target sequence and the antisense oligonucleotide are relative to the human TIGIT nucleic acid sequence set forth in SEQ ID NO: 1. The oligonucleotides shown in Table 1 have phosphorothioate (PS) linkages but may also include phosphodiester linkages. Those skilled in the art will recognize that other linkages, based on phosphodiester or non-phosphodiester moieties may be included.

TABLE 1

| Target sequence | SEQ ID NO: | Start site | Stop site | Antisense (5'-3') | SEQ ID NO: |
|---|---|---|---|---|---|
| cacaatagaaacaacggggaac | 27 | 151 | 172 | GTTCCCCGTTGTTTCTATTGTG | 2 |
| cctccaccacggcacaagtgac | 28 | 219 | 240 | GTCACTTGTGCCGTGGTGGAGG | 3 |
| caaggatcgagtggccccaggt | 29 | 319 | 340 | ACCTGGGGCCACTCGATCCTTG | 4 |
| ggccccaggtcccggcctgggc | 30 | 331 | 352 | GCCCAGGCCGGGACCTGGGCC | 5 |
| agtcgctgaccgtgaacgatac | 31 | 363 | 384 | GTATCGTTCACGGTCAGCGACT | 6 |
| gatgggacgtacactgggagaa | 32 | 419 | 440 | TTCTCCCAGTGTACGTCCCATC | 7 |
| catggccgcgacgctggtggtc | 33 | 511 | 532 | GACCACCAGCGTCGCGGCCATG | 8 |
| gtggtggtcgcgttgactagaa | 34 | 551 | 572 | TTCTAGTCAACGCGACCACCAC | 9 |
| actgtgccgagctgcatgacta | 35 | 719 | 740 | TAGTCATGCAGCTCGGCACAGT | 10 |
| tcagtgctgCGtgtgtgtgtgt | 36 | 889 | 910 | ACACACACACACGCAGCACTGA | 11 |
| gccttttCGttctattccattt | 37 | 979 | 1000 | AAATGGAATAGAACGAAAAGGC | 12 |
| tagggtgagtaaCGtggatctt | 38 | 1017 | 1038 | AAGATCCACGTTACTCACCCTA | 13 |
| tttcaCGtcattttcagtaatt | 39 | 1211 | 1232 | AATTACTGAAAATGACGTGAAA | 14 |
| ggaagagaCGacagtttggggt | 40 | 1407 | 1428 | ACCCCAAACTGTCGTCTCTTCC | 15 |
| ctcttccggccgtgtgtgctgg | 41 | 1682 | 1703 | CCAGCACACACGGCCGGAAGAG | 16 |
| ccaggaaacgcacatgcccaca | 42 | 1711 | 1732 | TGTGGGCATGTGCGTTTCCTGG | 17 |
| gccaagtcgtagcatttgggcc | 43 | 1739 | 1760 | GGCCCAAATGCTACGACTTGGC | 18 |
| agaaCGtttcccactaaaaaga | 44 | 1807 | 1828 | TCTTTTTAGTGGGAAACGTTCT | 19 |
| aacttcttcgaacccttttatt | 45 | 1919 | 1940 | AATAAAAGGGTTCGAAGAAGTT | 20 |
| cactccctgacgactttgtgct | 46 | 1941 | 1962 | AGCACAAAGTCGTCAGGGAGTG | 21 |
| ggtaactgaaccgcttatttct | 47 | 1971 | 1992 | AGAAATAAGCGGTTCAGTTACC | 22 |
| gaggaatgagcggggaggttgg | 48 | 2051 | 2072 | CCAACCTCCCCGCTCATTCCTC | 23 |
| aggttgtgtcttgcgcatggtt | 49 | 2131 | 2152 | AACCATGCGCAAGACACAACCT | 24 |
| attagatgaacgtaaaatgtt | 50 | 2339 | 2360 | AACATTTTTACGTTCATCTAAT | 25 |
| gacatgcgctatccaccacgtagc | 51 | 2739 | 2760 | GCTACGTGGTGGATAGCGCATGTC | 26 |

Certain embodiments provide a composition comprising an antisense oligonucleotide compound as described herein and a pharmaceutically acceptable carrier or diluent. Certain embodiments provide a composition comprising two or more compounds as described herein and a pharmaceutically acceptable carrier or diluent. The two or more compounds can be complementary to the same target region and/or segment or different target regions and/or segments of TIGIT.

In certain embodiments, the invention provides a composition comprising a compound according to the invention and a second agent including, but not limited to, one or more vaccines, antigens, antibodies, cytotoxic agents, chemotherapeutic agents (both traditional chemotherapy and modern targeted therapies), radiation, kinase inhibitors, allergens, antibiotics, agonist, antagonist, antisense oligonucleotides, ribozymes, RNAi molecules, siRNA molecules, miRNA molecules, aptamers, proteins, gene therapy vectors, DNA vaccines, adjuvants, co-stimulatory molecules or combinations thereof.

Certain embodiments provide compositions and methods comprising administering to an animal an antisense compound or composition disclosed herein. In certain embodiments, administering the antisense compound prevents, treats, ameliorates, or slows progression of cancer such as melanoma, head and neck squamous cell carcinoma, small cell or non-small cell lung carcinoma, hepatocellular carcinoma, breast cancer, cervical cancer, gastric cancer, colon rectal cancer, kidney cancer, esophageal squamous cell carcinoma, Merkel cell carcinoma, cutaneous squamous cell carcinoma, microsatellite instability high cancer or urothelial bladder cancer, inflammatory diseases such as systemic lupus erythematosus, systemic sclerosis, multiple sclerosis, rheumatoid arthritis, Crohn's disease, ulcerative colitis, non-alcoholic steatohepatitis and sepsis, and viral infection such as HIV, hepatitis B or hepatitis C.

Certain embodiments provide antisense compounds, compositions and methods as described herein for use in therapy to treat a TIGIT related disease, disorder or condition. In certain embodiments, TIGIT levels are elevated in an animal. In certain embodiments, the compound targeting TIGIT is used in treating, preventing, slowing progression, or ameliorating a disease, disorder or condition. In certain embodiments, the compositions and methods for therapy include administering a TIGIT specific inhibitor to an individual in need thereof.

Certain embodiments provide compositions and methods for reducing TIGIT levels. Certain embodiments provide compositions and methods to reduce TIGIT mRNA or protein expression in an animal comprising administering to the animal an antisense compound or composition disclosed herein to reduce TIGIT mRNA or protein expression in the animal.

In certain embodiments provided are methods for treating diseases or disorders that would benefit from the reduced expression of TIGIT, comprising administering to an animal a compound or composition as described herein to reduce TIGIT mRNA or protein expression in the animal. In certain embodiments, the animal is a human.

Certain embodiments provide compositions and methods for preventing, treating, delaying, slowing the progression and/or ameliorating TIGIT related diseases, disorders, and conditions in a subject in need thereof. In certain embodiments, such diseases, disorders, and conditions include cancer, inflammatory diseases and viral infection. Certain such cancers include, but are not limited to, melanoma, head and neck squamous cell carcinoma, small cell and non-small cell lung carcinoma, hepatocellular carcinoma, gastroesophageal, breast cancer, cervical cancer, gastric cancer, colon rectal carcinoma, kidney cancer, esophageal squamous cell carcinoma, Merkel cell carcinoma, cutaneous squamous cell carcinoma, microsatellite instability high cancer or urothelial bladder and urinary tract and renal cell carcinoma. Certain embodiments provide compositions and methods for preventing, treating, delaying, slowing the progression and/or ameliorating cancer.

In certain embodiments, the modulation of TIGIT expression occurs in a cell, tissue or organ. In certain embodiments, the modulations occur in a cell, tissue or organ in an animal. In certain embodiments, the modulation is a reduction in TIGIT mRNA level. In certain embodiments, the modulation is a reduction in TIGIT protein level. In certain embodiments, both TIGIT mRNA and protein levels are reduced. Such reduction may occur in a time-dependent or in a dose-dependent manner.

In certain embodiments, the subject or animal is human.

In any of the methods according to the invention, administration of compounds according to the invention, alone or in combination with any other agent, can be by any suitable route, including, without limitation, intramuscular, parenteral, mucosal, oral, sublingual, intratumoral, transdermal, topical, inhalation, intrathecal, intranasal, aerosol, intraocular, intratracheal, intrarectal, vaginal, by gene gun, dermal patch or in eye drop or mouthwash form. In any of the methods according to the invention, administration of compounds according to the invention, alone or in combination with any other agent, can be directly to a tissue or organ such as, but not limited to, the bladder, liver, lung, kidney or lung. In certain embodiments, administration of compounds according to the invention, alone or in combination with any other agent, is by intramuscular administration. In certain embodiments, administration of gene silencing compounds according to the invention, alone or in combination with any other agent, is by mucosal administration. In certain embodiments, administration of gene silencing compounds according to the invention, alone or in combination with any other agent, is by oral administration. In certain embodiments, administration of gene silencing compounds according to the invention, alone or in combination with any other agent, is by intratumoral administration.

In certain embodiments, the antisense compound is parenterally administered. In further embodiments, the parenteral administration is subcutaneous.

In certain embodiments, the antisense compound or composition is co-administered with a second agent or therapy. In certain embodiments, the antisense compound or composition and the second agent are administered concomitantly.

In certain embodiments, the second agent includes, but not limited to, one or more vaccines, antigens, antibodies, cytotoxic agents, chemotherapeutic agents (both traditional chemotherapy and modern targeted therapies), kinase inhibitors, allergens, antibiotics, agonist, antagonist, antisense oligonucleotides, ribozymes, RNAi molecules, siRNA molecules, miRNA molecules, aptamers, peptides, targeted therapeutic agents, proteins, gene therapy vectors, DNA vaccines, adjuvants, co-stimulatory molecules or combinations thereof. Agents or therapies can be co-administered or administered concomitantly. Agents or therapies can be sequentially or subsequently administered.

Certain embodiments provide use of an antisense compound targeted to TIGIT for decreasing TIGIT levels in an animal. Certain embodiments provide use of an antisense compounds targeted to TIGIT for the treatment, prevention, or amelioration of a disease, disorder, or condition associated with TIGIT.

Certain embodiments provide use of an antisense compound targeted to TIGIT in the preparation of a medicament for decreasing TIGIT levels in an animal. Certain embodiments provide use of an antisense compound for the preparation of a medicament for the treatment, prevention, or amelioration of a disease, disorder, or condition associated with TIGIT.

Administration of the therapeutic compositions of compounds according to the invention can be carried out using known procedures using an effective amount and for periods of time effective to reduce symptoms or surrogate markers of the disease. For example, an effective amount of a compound according to the invention for treating a disease and/or disorder could be that amount necessary to alleviate or reduce the symptoms, or delay or ameliorate the disease and/or disorder. In the context of administering a composition that modulates gene expression, an effective amount of a compound according to the invention is an amount sufficient to achieve the desired modulation as compared to the gene expression in the absence of the compound according to the invention. The effective amount for any particular application can vary depending on such factors as the disease or condition being treated, the particular compound being administered, the size of the subject, or the severity of the disease or condition. One of ordinary skill in the art can empirically determine the effective amount of a particular compound without necessitating undue experimentation.

When administered systemically, the therapeutic composition is preferably administered at a sufficient dosage to attain a blood level of compound according to the invention from about 0.0001 micromolar to about 10 micromolar. For localized administration, much lower concentrations than this may be effective, and much higher concentrations may be tolerated. Preferably, a total dosage of compound according to the invention ranges from about 0.001 mg per patient per day to about 200 mg per kg body weight per day. In certain embodiments, the total dosage may be 0.08, 0.16, 0.32, 0.48, 0.32, 0.64, 1, 10 or 30 mg/kg body weight administered daily, twice weekly or weekly. It may be desirable to administer simultaneously, or sequentially a therapeutically effective amount of one or more of the therapeutic compositions of the invention to an individual as a single treatment episode.

The methods according to this aspect of the invention are useful for model studies of gene expression. The methods are also useful for the prophylactic or therapeutic treatment of human or animal disease. For example, the methods are useful for pediatric and veterinary inhibition of gene expression applications.

Certain embodiments provide a kit for treating, preventing, or ameliorating a disease, disorder or condition as described herein wherein the kit comprises: (i) a TIGIT specific inhibitor as described herein; and optionally (ii) a second agent or therapy as described herein. A kit of the present invention can further include instructions for using the kit to treat, prevent, or ameliorate a disease, disorder or condition as described herein.

EXAMPLE(S)

The following examples illustrate certain embodiments of the present disclosure and are not limiting. Moreover, where specific embodiments are provided, the inventors have contemplated generic application of those specific embodiments.

Example 1—Synthesis of Antisense Oligonucleotides

All oligonucleotides are synthesized on a 10-μmole scale using β-cyanoethylphosphoramidite chemistry on a solid support using automated DNA/RNA synthesizers (Mermade 6, BioAutomation, Tex.). The phosphoramidites of dA, dC, dG and T are sequentially coupled on desired sequences on an automated DNA/RNA synthesizer. The crude oligonucleotides are deprotected and cleaved from the solid support by treating concentrate ammonium hydroxide at 55° C. for overnight. The crude oligonucleotides are purified by a preparative anion exchange HPLC. The purified oligonucleotides are desalted from Cis column and dialyzed against large volume of sterile water for overnight. Oligonucleotide solution is filtrated with a sterilized filter (0.2 μm or 0.45 μm HT Tuffryn Membrane, Pall Corporation) and then lyophilized for final product. All oligonucleotides are characterized by IE-HPLC (Waters 600, Waters 486 Tunable Absorbance Detector at 260 nm, Empower software) and MALDI-TOF mass spectrometry (Waters MALDI-ToF mass spectrometer with 337 nm $N_2$ laser) for purity and molecular mass, respectively. The purity of full-length oligonucleotides ranged from 95-98%, with the remainder lacking one or two nucleotides, as determined by ion-exchange HPLC. All oligonucleotides were tested for endotoxin levels by the Limulus assay (Bio-Whittaker) and contained <0.1 EU/mg.

Example 2—In Vitro Screening of TIGIT Antisense Oligonucleotides

To identify potent human TIGIT antisense, antisense oligonucleotides (ASOs) targeting human TIGIT mRNA were screened in human HeLa and/or NTERA-2 cell lines (ATCC, Manassas, Va.) to assess human TIGIT mRNA expression compared to a scrambled control oligonucleotide. $5 \times 10^5$ cells were seeded in 12 well tissue culture plate and incubated overnight at 37° C., 5% $CO_2$. On the day of transfection, fresh medium was added to each well. Antisense oligonucleotides were prepared at 25 and 50 nM concentration in 50 μl serum free medium and mixed with 50 μl serum free medium containing 3 μl of lipofectamine 2000® (Thermo Fisher Scientific, Waltham, Mass.). The mixture was incubated at room temperature for 10 minutes and then applied to culture plates. Plates were then incubated for 48 hours at 37° C., 5% $CO_2$. Total RNA was isolated using RNeasy Mini (Qiagen, Germantown, Md.) according to manufacturer's suggestion. RNA concentration was determined by UV spectrophotometer at 260/280 nm wavelength. For cDNA synthesis, 1 μg of total RNA was transcribed using High-Capacity cDNA Reverse Transcription kit (Thermo Fisher Scientific) according to manufacturer's suggestion. Human TIGIT mRNA expression level was determined by real-time quantitative PCR. Briefly, about 75 μg cDNA was mixed with 10 μl of TaqMan™ Fast Advanced Master Mix (Thermo Fisher Scientific) and 1 μl human TIGIT gene expression probe (Hs00545087_m1, Thermo Fisher Scientific) or 1 μl human HPRT1 gene expression probe (Hs02800695_m1, Thermo Fisher Scientific). Real-time quantitative PCR was performed using a StepOnePlus™ Real-Time PCR system (Thermo Fisher Scientific) and relative TIGIT gene expression was calculated using StepOne software version 2 (Thermo Fisher Scientific). Results are shown in Table 2.

TABLE 2

| Human TIGIT antisense | % TIGIT expression knockdown Antisense oligo concentration | |
|---|---|---|
| | 25 nM | 50 nM |
| SEQ ID NO: 2 | 15 | 59 |
| SEQ ID NO: 3 | 3 | 0 |
| SEQ ID NO: 4 | 46 | 79 |
| SEQ ID NO: 5 | 5 | 35 |
| SEQ ID NO: 6 | 56 | 70 |
| SEQ ID NO: 7 | 24 | 65 |
| SEQ ID NO: 8 | 22 | 53 |
| SEQ ID NO: 9 | 40 | 74 |
| SEQ ID NO: 10 | 15 | 55 |
| SEQ ID NO: 11 | 39 | 70 |
| SEQ ID NO: 12 | 17 | 64 |
| SEQ ID NO: 13 | 50 | 78 |
| SEQ ID NO: 14 | 9 | 49 |
| SEQ ID NO: 15 | 14 | 47 |
| SEQ ID NO: 16 | 0 | 0 |
| SEQ ID NO: 17 | 0 | 7 |
| SEQ ID NO: 18 | 15 | 51 |
| SEQ ID NO: 19 | 0 | 21 |
| SEQ ID NO: 20 | 5 | 0 |
| SEQ ID NO: 21 | 0 | 0 |
| SEQ ID NO: 22 | 10 | 0 |
| SEQ ID NO: 23 | 6 | 17 |
| SEQ ID NO: 24 | 38 | 67 |
| SEQ ID NO: 25 | 13 | 45 |
| SEQ ID NO: 26 | 10 | 5 |

A mouse TIGIT antisense oligonucleotide (mTIGIT ASO) (5'-GCTGTCGTTAGCCAGTCTTCGATAC-3')(SEQ ID NO: 53) was used to assess the effect on mouse TIGIT mRNA expression in mouse CT26.CL25 cell line (ATCC). $5 \times 10^5$ cells were seeded in 12 well tissue culture plate and incubated overnight at 37° C., 5% $CO_2$. On the day of transfection, fresh medium was added to each well. Antisense oligonucleotides were prepared at 0.21, 0.62, 1.85, 5.56, 16.67 and 50 nM concentration in 50 µl serum free medium and mixed with 50 µl serum free medium containing 3 µl of lipofectamine 2000® (Thermo Fisher Scientific). The mixture was incubated at room temperature for 10 minutes and then applied to culture plates. Plates were then incubated for 48 hours at 37° C., 5% $CO_2$. Total RNA was isolated using RNeasy Mini (Qiagen) according to manufacturer's suggestion. RNA concentration was determined by UV spectrophotometer at 260/280 nm wavelength. For cDNA synthesis, 1 µg of total RNA was transcribed using High Capacity cDNA (Thermo Fisher Scientific) according to manufacturer's suggestion. Mouse TIGIT mRNA expression level was determined by real-time quantitative PCR. Briefly, about 75 µg cDNA was mixed with 10 µl of Fast TaqMan assay buffer (Thermo Fisher Scientific) and 1 µl mouse TIGIT gene expression probe (Mm03807522_m1, Thermo Fisher Scientific) or 1 µl mouse HPRT1 gene expression probe (Mm01324427_m1, Thermo Fisher Scientific). Real-time quantitative PCR was performed using a StepOnePlus PCR machine (Thermo Fisher Scientific) and relative TIGIT gene expression was calculated using StepOne software version 2 (Thermo Fisher Scientific). A mouse TIGIT antisense oligonucleotide (mTIGIT ASO) analog showed potent mouse TIGIT mRNA inhibition in a mouse CT26.CL25 cell line. (FIG. 1).

Example 3—In Vivo Experiments Evaluating Antitumor Activity by TIGIT Inhibition

To ascertain knockdown of TIGIT by an ASO can impact T cell and NK cell function, a murine analog of hTIGIT was evaluated in murine tumor models alone or in combination with anti-PD-1 antibody.

Figures 2A, 2B:
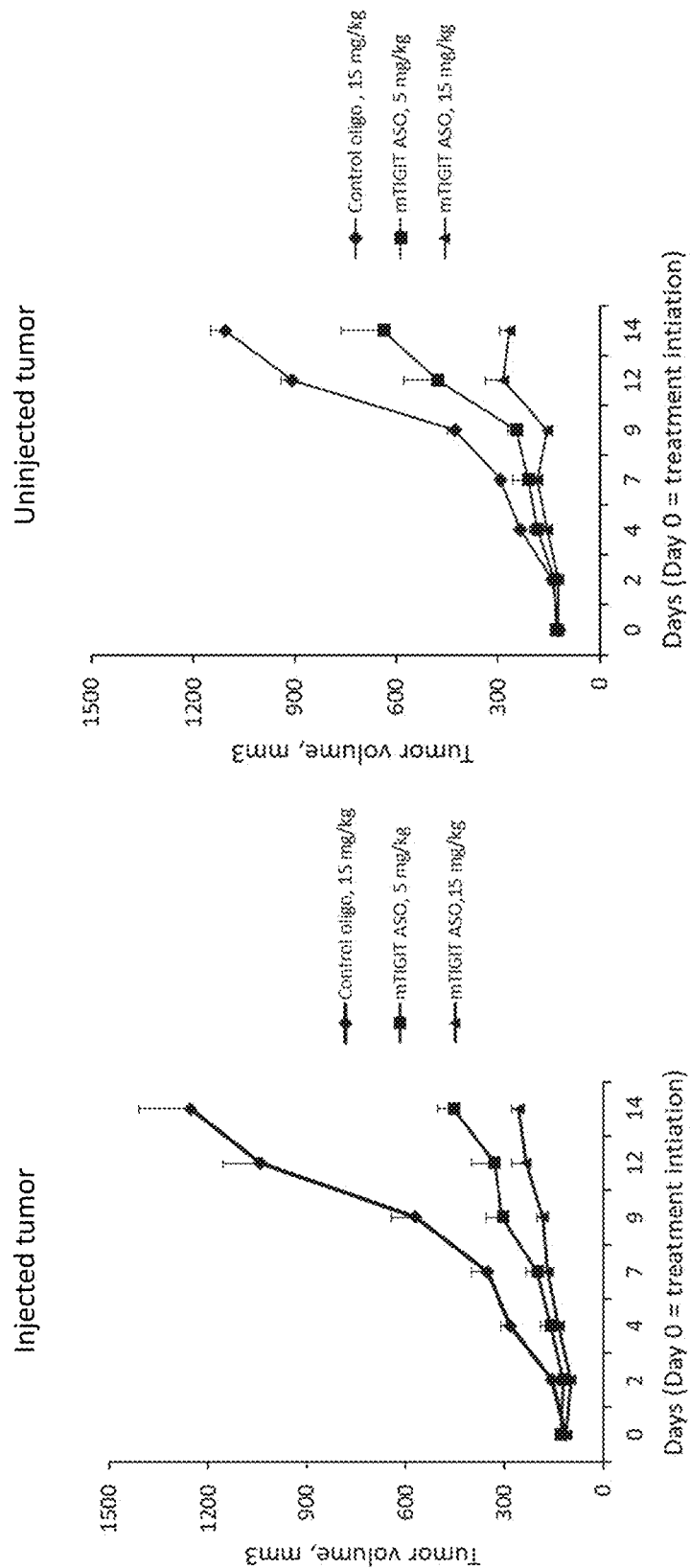
FIG. 2A and FIG. 2B demonstrate that TIGIT antisense dose dependently inhibits tumor growth in vivo.
Figure 3B:
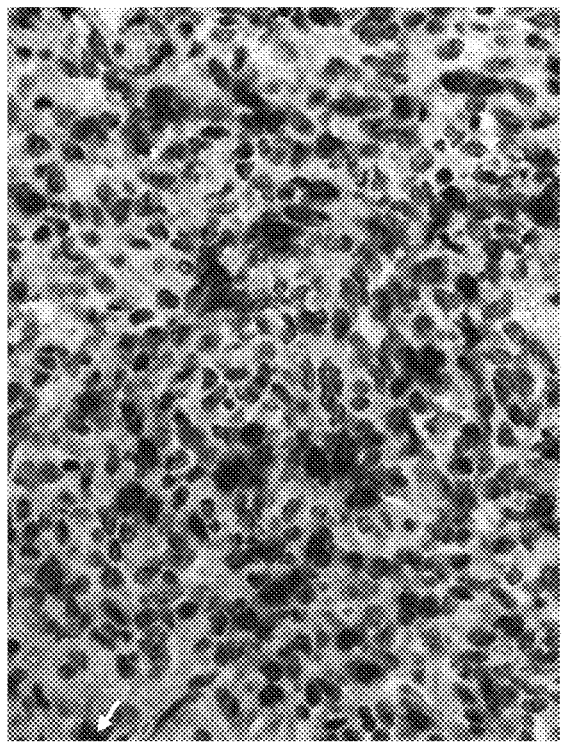
FIG. 3 demonstrates TIGIT antisense increases tumor infiltrating $CD3^+$ T cells.
Figure 3A:
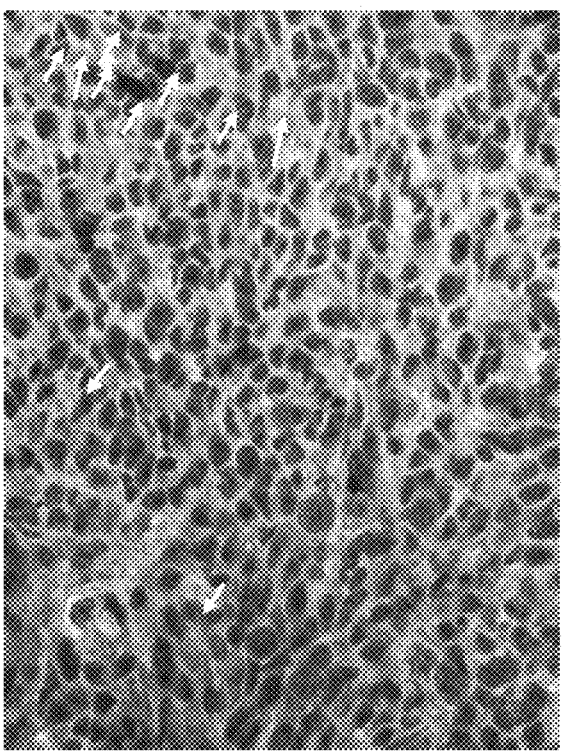

A mouse CT26.CL25 tumor model was employed to assess the in vivo effects of mouse TIGIT inhibition. BALB/c female mice, 6-8 weeks old were injected subcutaneously with $3 \times 10^6$ murine colon carcinoma CT26.CL25 (ATCC) cells into both flanks to establish solid tumors. Treatment was initiated at day 4 after tumor implantation when the tumor volume reached between 50 and 150 $mm^3$. Tumor-bearing mice were randomly divided into 3 treatment groups (n=10 mice/group). Control oligo (15 mg/kg), 5 or 15 mg/kg mTIGIT ASO in 100 µl PBS were administrated by intratumoral injection (i.t) into the right flank tumor for total of 5 times on days 4, 7, 11, 13 and 15. Tumor volume was calculated based on twice weekly caliper measurement using the formula: volume=$(width)^2 \times length/2$.-Tumor bearing mice treated with mTIGIT ASO showed a dose dependent tumor growth inhibition in both injected and uninjected tumor (FIG. 2). Tumor samples from 15 mg/kg mTIGIT ASO and control oligo treated groups were collected at day 15 and stored in 10% buffered formalin. Tissue sections were prepared by Mass Histology Service (Worcester, Mass.) and stained for CD3+ T cells using an anti-mouse CD3 antibody. The inhibition of mouse TIGIT expression led to an increase of tumor infiltrating CD3+ T lymphocytes (indicated by white arrows) when compared to a control oligo injected tumor (FIG. 3).

TIGIT has been reported to be expressed primarily on NK and some T cells[1]. Given the function of TIGIT as a negative regulator of NK and T cell immune function[1,2], inhibiting TIGIT may lead to the activation of such cell populations. To evaluate the effect of TIGIT ASO on NK and CD8+ T cell function, a murine tumor model was studied where NK or CD8+ T cells were depleted. BALB/c mice were injected subcutaneously with $3 \times 10^6$ murine colon carcinoma CT26.CL25 cells into the right flank at day 0 to establish solid tumors. NK cells or CD8+ T cells were depleted by intraperitoneal injection of 50 µl of Ultra-LEAF™ Purified anti-Asialo-GM1 Antibody (n=10, Biolegend, San Diego, Calif.) or 25 mg/kg anti-mouse CD8 monoclonal antibody (n=8, clone YTS 169.4; cat. no. BE0117, BioXcell, West Lebanon, N.H.), respectively on days −1, 4, 8 and 12. Tumor-bearing mice without cell depletion (n=10), NK- or CD8+-depleted tumor-bearing mice were treated by intratumoral injection of 15 mg/kg for total of 5 times on days 5, 8, 11, 12 and 13. Depletion of NK or CD8+ cells have no impact on tumor growth. Naïve tumor-bearing mice were intratumorally injected with 15 mg/kg control oligo with same injection schedule. Tumor volume was calculated based on twice weekly caliper measurement using the formula: volume=$(width)^2 \times length/2$.

Figure 4A:
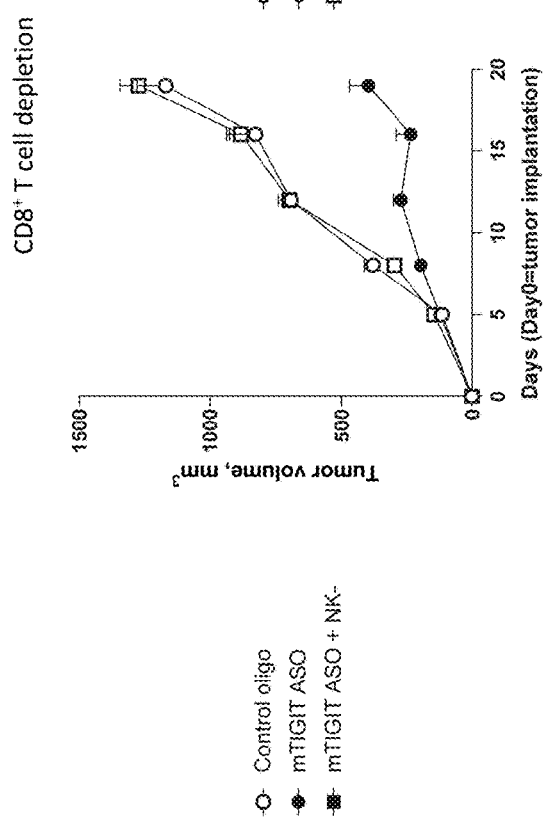
FIG. 4A through FIG. 4C demonstrate the anti-tumor effect of TIGIT antisense is dependent on NK and $CD8^+$ T cells.
Figure 4B:
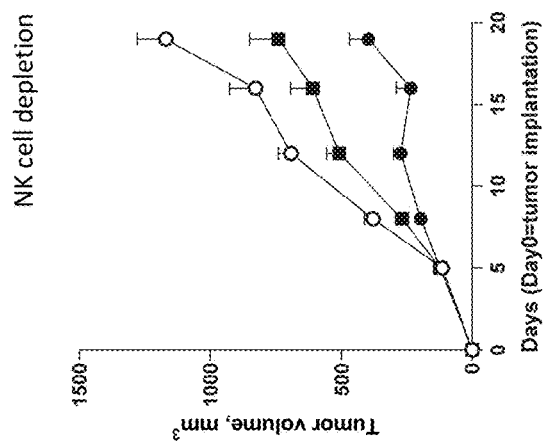
Figure 4C:
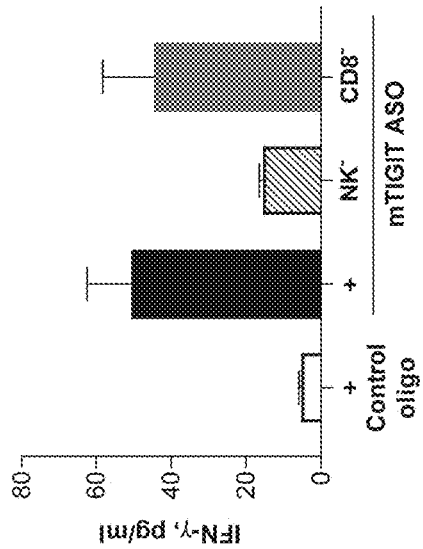

Plasma samples collected 2 days after last mTIGIT ASO or control oligo treatment were analyzed by ELISA for interferon-γ level. ELISA assay was performed using a mouse IFN-gamma Quantikine ELISA Kit (R&D Systems, Minneapolis, Minn.) according to manufacturer's suggestions. The tumor growth inhibition effects of mTIGIT ASO was abolished in NK (FIG. 4A) and CD8+ cell (FIG. 4B) depleted tumor bearing mice. This further supports that mTIGIT ASO targets TIGIT gene expression (which is expressed on NK and some T cells, including CD8+ T cells). Furthermore, treatment with mTIGIT ASO resulted in increased production of IFN-γ, a key NK cell cytokine (FIG. 4C). This increased of IFN-γ production from TIGIT inhibition is abolished by depleting NK cells but not by depleting CD8⁺ T cells (FIG. 4C). This further supports that mTIGIT ASO inhibits TIGIT expression and activates NK cells.

Figure 5:
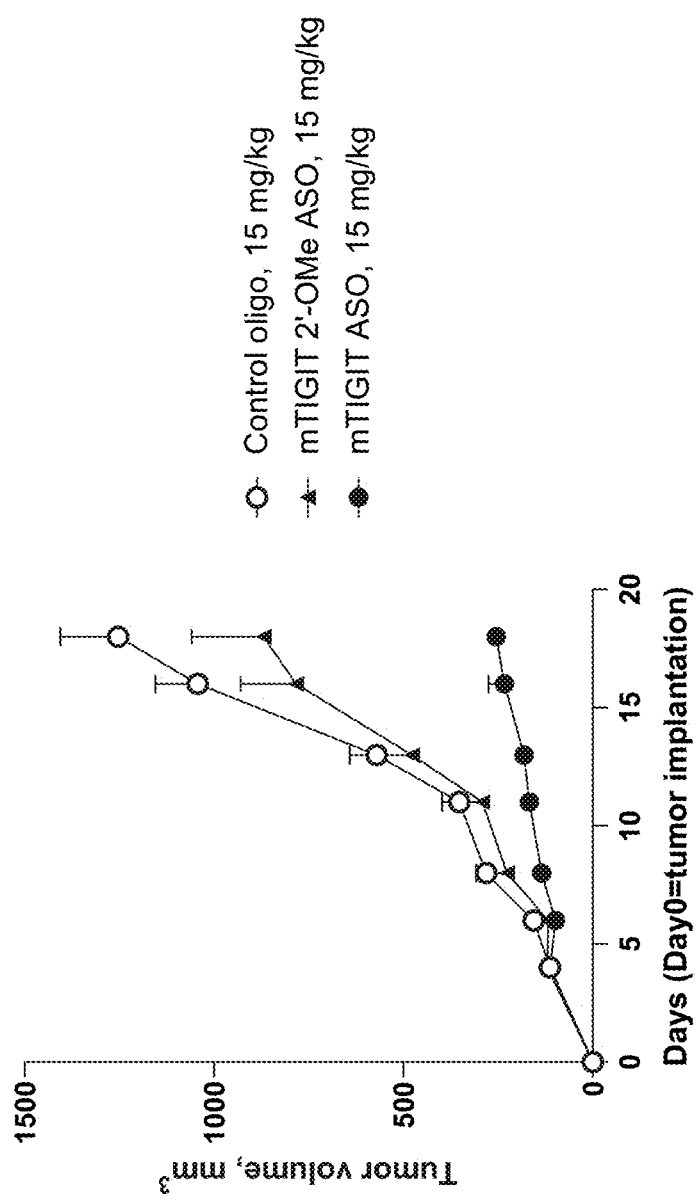
FIG. 5 demonstrates that local injection of ASOs does not require chemical modifications of oligonucleotides.

Based on the above, and without wishing to be bound to any particular theory, it was believed that for local administration, an unmodified ASO will have an advantage over modified ASOs because the charge of the unmodified ASO may result in more residence time at local sites. To evaluate this hypothesis, 5 oligonucleotides were modified at both the 5' and 3' end of mTIGIT ASO to 2'-O-Methyl ribonucleotides and compared its antitumor activity with its original version. BALB/c female mice, 6-8 weeks old were injected subcutaneously with $3 \times 10^6$ murine colon carcinoma CT26.CL25 (ATCC) cells into the right flank to establish solid tumors. Treatment was initiated at day 4 after tumor implantation when the tumor volume reached between 50 and 150 mm³. Tumor-bearing mice were randomly divided into 3 treatment groups (n=10 mice/group). Control oligo (15 mg/kg), 15 mg/kg mTIGIT ASO or 15 mg/kg mTIGIT 2'-OMe ASO (where 5 mTIGIT 2'-OMe ASOs in 100 μl PBS were administered by intratumoral injection (i.t) into the tumor for total of 5 times on days 4, 7, 11, 13 and 15. Tumor volume was calculated based on twice weekly caliper measurement using the formula: volume=(width)²×length/2. Although 2'-O-Methyl modification still have some antitumor activity, its potency was much reduced (FIG. 5) suggesting that unmodified antisense may be more suitable in intratumoral administration compared to 2'-O-Methyl or 2'-O-Methoxyethyl modified antisense oligo.

Figure 6B:
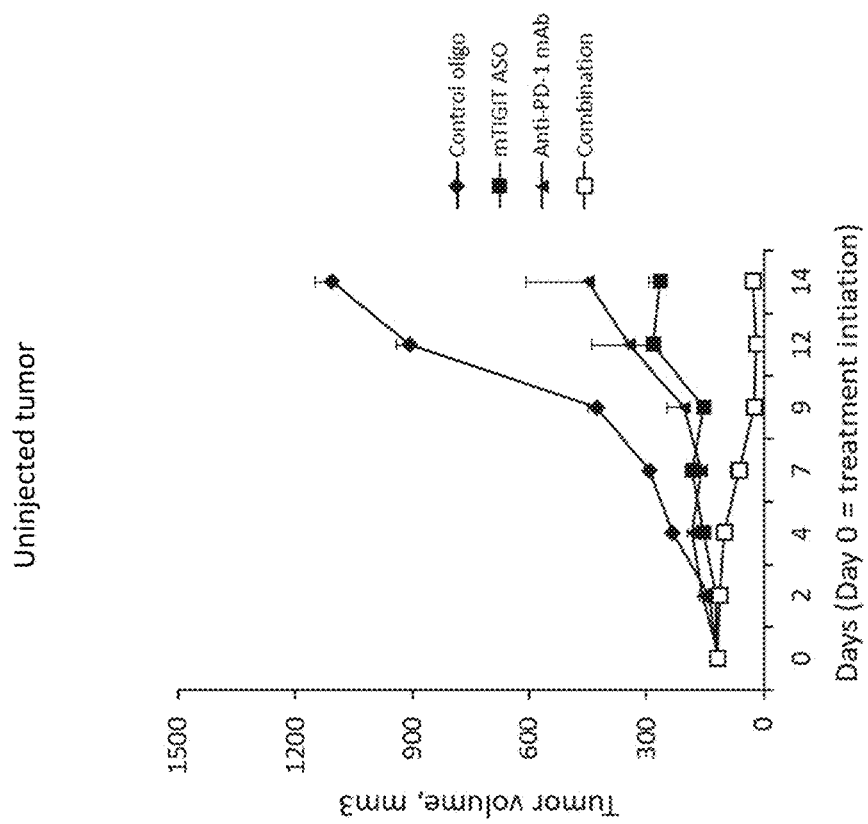
FIG. 6A and FIG. 6B demonstrate treatment with TIGIT antisense in combination with anti-PD-1 antibody synergistically inhibits tumor growth.
Figure 6A:
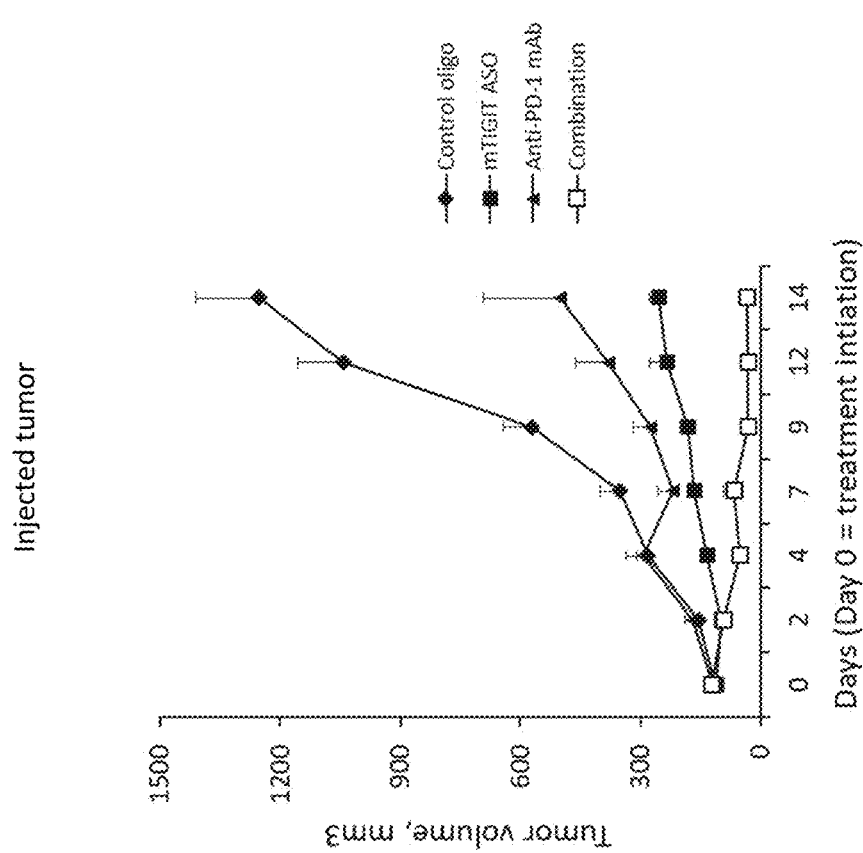

Inhibition of TIGIT can reactivate NK and T cells, therefore provides a therapeutic advantage when combined with other checkpoint inhibitors in treating cancer comparing to checkpoint inhibitor monotherapy. A synergistic tumor growth inhibition was observed when both mTIGIT and PD-1 were targeted in a mouse tumor model (FIG. 6).

REFERENCES

1. Yu X et al., 2009. The surface protein TIGIT suppresses T cell activation by promoting the generation of mature immunoregulatory dendritic cells. Nat Immunol. 10: 48-57.
2. Stanietsky N et al., 2009. The interaction of TIGIT with PVR and PVRL2 inhibits human NK cell cytotoxicity. Proc Natl Acad Sci USA. 106: 17858-63.
3. Chew G M et al., 2016. TIGIT Marks Exhausted T Cells, Correlates with Disease Progression, and Serves as a Target for Immune Restoration in HIV and SIV Infection. PLoS Pathogens. 12: e1005349.
4. Guillerey C et al., 2018. TIGIT immune checkpoint blockade restores CD8⁺ T cell immunity against multiple myeloma. Blood 2018: blood-2018-01-825265; doi: https://doi.org/10.1182/blood-2018-01-825265.
5. Chauvin J et al., 2015. TIGIT and PD-1 impair tumor antigen-specific CD8⁺ T cells in melanoma patients. J Clin Invest. 125: 2046-2058.
6. Pauken K E and Wherry E J. 2014. TIGIT and CD226: tipping the balance between co-stimulatory and coinhibitory molecules to augment the cancer immunotherapy toolkit. Cancer Cell 26:785-787.

What is claimed:

1. A synthetic modified oligonucleotide compound comprising a nucleotide sequence of SEQ ID NO: 6.

2. A composition comprising a compound according to claim 1 and a pharmaceutically acceptable carrier.

3. The composition according to claim 2, further comprising one or more vaccines, antigens, antibodies, cytotoxic agents, chemotherapeutic agents (both traditional chemotherapy and modern targeted therapies), radiation, kinase inhibitors, allergens, antibiotics, agonist, antagonist, antisense oligonucleotides, ribozymes, RNAi molecules, siRNA molecules, miRNA molecules, aptamers, proteins, gene therapy vectors, DNA vaccines, adjuvants, co-stimulatory molecules or combinations thereof.

4. A method for inhibiting TIGIT mRNA or protein expression in vitro, the method comprising contacting a cell with at least one compound according to claim 1.

* * * * *

SEQUENCE LISTING

<160> NUMBER OF SEQ ID NOS: 53

<210> SEQ ID NO 1
<211> LENGTH: 2978
<212> TYPE: DNA
<213> ORGANISM: Artificial Sequence
<220> FEATURE:
<223> OTHER INFORMATION: Synthetic Oligonucleotide

<400> SEQUENCE: 1

```
cgtcctatct gcagtcggct actttcagtg gcagaagagg ccacatctgc ttcctgtagg    60
ccctctgggc agaagcatgc gctggtgtct cctcctgatc tgggcccagg ggctgaggca   120
ggctcccctc gcctcaggaa tgatgacagg cacaatagaa caacgggga acatttctgc   180 agagaaaggt ggctctatca tcttacaatg tcacctctcc tccaccacgg cacaagtgac   240
ccaggtcaac tgggagcagc aggaccagct tctggccatt tgtaatgctg acttggggtg   300
gcacatctcc ccatccttca aggatcgagt ggccccaggt cccggcctgg gcctcaccct   360
ccagtcgctg accgtgaacg atacagggga gtacttctgc atctatcaca cctaccctga   420
tgggacgtac actgggagaa tcttcctgga ggtcctagaa agctcagtgg ctgagcacgg   480
tgccaggttc cagattccat tgcttggagc catggccgcg acgctggtgg tcatctgcac   540
agcagtcatc gtggtggtcg cgttgactag aaagaagaaa gccctcagaa tccattctgt   600
ggaaggtgac ctcaggagaa aatcagctgg acaggaggaa tggagcccca gtgctccctc   660 accccagga agctgtgtcc aggcagaagc tgcacctgct gggctctgtg gagagcagcg   720
gggagaggac tgtgccgagc tgcatgacta cttcaatgtc ctgagttaca gaagcctggg   780
```

```
taactgcagc ttcttcacag agactggtta gcaaccagag gcatcttctg gaagatacac    840
ttttgtcttt gctattatag atgaatatat aagcagctgt actctccatc agtgctgcgt    900
gtgtgtgtgt gtgtgtatgt gtgtgtgtgt tcagttgagt gaataaatgt catcctcttc    960
tccatcttca tttccttggc cttttcgttc tattccattt tgcattatgg caggcctagg   1020
gtgagtaacg tggatcttga tcataaatgc aaaattaaaa aatatcttga cctggttta    1080
aatctggcag tttgagcaga tcctatgtct ctgagagaca cattcctcat aatggccagc   1140
attttgggct acaaggtttt gtggttgatg atgaggatgg catgactgca gagccatcct   1200
catctcattt tttcacgtca ttttcagtaa cttttcactca ttcaaaggca ggttataagt   1260
aagtcctggt agcagcctct atggggagat ttgagagtga ctaaatcttg gtatctgccc   1320
tcaagaactt acagttaaat ggggagacaa tgttgtcatg aaaaggtatt atagtaagga   1380
gagaaggaga catacacagg ccttcaggaa gagacgacag tttggggtga ggtagttggc   1440
ataggcttat ctgtgatgaa gtggcctggg agcaccaagg ggatgttgag gctagtctgg   1500
gaggagcagg agttttgtct agggaacttg taggaaattc ttggagctga aagtcccaca   1560
aagaaggccc tggcaccaag ggagtcagca aacttcagat tttattctct gggcaggcat   1620
ttcaagtttc cttttgctgt gacatactca tccattagac agcctgatac aggcctgtag   1680
cctcttccgg ccgtgtgtgc tggggaagcc ccaggaaacg cacatgccca cacagggagc   1740
caagtcgtag catttgggcc ttgatctacc ttttctgcat caatacactc ttgagccttt   1800
gaaaaagaa cgtttcccac taaaagaaa atgtggattt ttaaaatagg gactcttcct   1860
agggaaaaa ggggggctgg gagtgataga gggtttaaaa aataaacacc ttcaaactaa   1920
cttcttcgaa ccctttttatt cactccctga cgactttgtg ctggggttgg ggtaactgaa   1980
ccgcttattt ctgtttaatt gcattcaggc tggatcttag aagacttta tccttccacc   2040
atctctctca gaggaatgag cggggaggtt ggatttactg gtgactgatt ttctttcatg   2100
ggccaaggaa ctgaaagaga atgtgaagca aggttgtgtc ttgcgcatgg ttaaaaataa   2160
agcattgtcc tgcttcctaa gacttagact ggggttgaca attgttttag caacaagaca   2220
attcaactat ttctcctagg attttttatta ttattatttt ttcacttttc taccaaatgg   2280
gttacatagg aagaatgaac tgaaatctgt ccagagctcc aagtcctttg gaagaaagat   2340
tagatgaacg taaaaatgtt gttgtttgct gtggcagttt acagcatttt tcttgcaaaa   2400
ttagtgcaaa tctgttggaa atagaacaca attcacaaat tggaagtgaa ctaaaatgta   2460
atgacgaaaa gggagtagtg ttttgatttg gaggaggtgt atattcggca gaggttggac   2520
tgagagttgg gtgttattta acataattat ggtaattggg aaacatttat aaacactatt   2580
gggatggta taaatacaa aagggcctat agatgttaga aatgggtcag gttactgaaa   2640
tgggattcaa tttgaaaaaa atttttttaa atagaactca ctgaactaga ttctcctctg   2700
agaaccagag aagaccattt catagttgga ttcctggaga catgcgctat ccaccacgta   2760
gccactttcc acatgtggcc atcaaccact taagatgggg ttagtttaaa tcaagatgtg   2820
ctgttataat tggtataagc ataaaatcac actagattct ggagatttaa tatgaataat   2880
aagaatacta tttcagtagt tttggtatat tgtgtgtcaa aaatgataat attttggatg   2940
tattgggtga aataaaatat taacattaaa aaaaaaaa                           2978

<210> SEQ ID NO 2
<211> LENGTH: 22
<212> TYPE: DNA
<213> ORGANISM: Artificial Sequence
```

```
<220> FEATURE:
<223> OTHER INFORMATION: Synthetic Oligonucleotide

<400> SEQUENCE: 2
gttccccgtt gtttctattg tg                                              22

<210> SEQ ID NO 3
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 3
gtcacttgtg ccgtggtgga gg                                              22

<210> SEQ ID NO 4
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 4
acctggggcc actcgatcct tg                                              22

<210> SEQ ID NO 5
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 5
gcccaggccg ggacctgggg cc                                              22

<210> SEQ ID NO 6
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 6
gtatcgttca cggtcagcga ct                                              22

<210> SEQ ID NO 7
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 7
ttctcccagt gtacgtccca tc                                              22

<210> SEQ ID NO 8
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 8
gaccaccagc gtcgcggcca tg                                              22
```

```
<210> SEQ ID NO 9
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 9
ttctagtcaa cgcgaccacc ac                                              22

<210> SEQ ID NO 10
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 10
tagtcatgca gctcggcaca gt                                              22

<210> SEQ ID NO 11
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 11
acacacacac acgcagcact ga                                              22

<210> SEQ ID NO 12
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 12
aaatggaata gaacgaaaag gc                                              22

<210> SEQ ID NO 13
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 13
aagatccacg ttactcaccc ta                                              22

<210> SEQ ID NO 14
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 14
aattactgaa aatgacgtga aa                                              22

<210> SEQ ID NO 15
<211> LENGTH: 22
<212> TYPE: DNA
<213> ORGANISM: Artificial Sequence
<220> FEATURE:
<223> OTHER INFORMATION: Synthetic Oligonucleotide
```

<400> SEQUENCE: 15
accccaaact gtcgtctctt cc                                              22

<210> SEQ ID NO 16
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 16
ccagcacaca cggccggaag ag                                              22

<210> SEQ ID NO 17
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 17
tgtgggcatg tgcgtttcct gg                                              22

<210> SEQ ID NO 18
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 18
ggcccaaatg ctacgacttg gc                                              22

<210> SEQ ID NO 19
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 19 tcttttttagt gggaaacgtt ct                                             22

<210> SEQ ID NO 20
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 20
aataaaaggg ttcgaagaag tt                                              22

<210> SEQ ID NO 21
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 21
agcacaaagt cgtcagggag tg                                              22

<210> SEQ ID NO 22

```
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 22
agaaataagc ggttcagtta cc                                              22

<210> SEQ ID NO 23
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 23
ccaacctccc cgctcattcc tc                                              22

<210> SEQ ID NO 24
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 24
aaccatgcgc aagacacaac ct                                              22

<210> SEQ ID NO 25
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 25
aacattttta cgttcatcta at                                              22

<210> SEQ ID NO 26
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 26
gctacgtggt ggatagcgca tgtc                                            24

<210> SEQ ID NO 27
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 27
cacaatagaa acaacgggga ac                                              22

<210> SEQ ID NO 28
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 28
```

```
cctccaccac ggcacaagtg ac                                               22

<210> SEQ ID NO 29
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 29
caaggatcga gtggccccag gt                                               22

<210> SEQ ID NO 30
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 30
ggccccaggt cccggcctgg gc                                               22

<210> SEQ ID NO 31
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 31
agtcgctgac cgtgaacgat ac                                               22

<210> SEQ ID NO 32
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 32
gatgggacgt acactgggag aa                                               22

<210> SEQ ID NO 33
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 33
catggccgcg acgctggtgg tc                                               22

<210> SEQ ID NO 34
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 34
gtggtggtcg cgttgactag aa                                               22

<210> SEQ ID NO 35
<211> LENGTH: 22
<212> TYPE: DNA
```

```
<213> ORGANISM: Artificial Sequence
<220> FEATURE:
<223> OTHER INFORMATION: Synthetic Oligonucleotide

<400> SEQUENCE: 35
actgtgccga gctgcatgac ta                                              22

<210> SEQ ID NO 36
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 36
tcagtgctgc gtgtgtgtgt gt                                              22

<210> SEQ ID NO 37
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 37
gccttttcgt tctattccat tt                                              22

<210> SEQ ID NO 38
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 38
tagggtgagt aacgtggatc tt                                              22

<210> SEQ ID NO 39
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 39
tttcacgtca ttttcagtaa tt                                              22

<210> SEQ ID NO 40
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 40
ggaagagacg acagtttggg gt                                              22

<210> SEQ ID NO 41
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 41
ctcttccggc cgtgtgtgct gg                                              22
```

<210> SEQ ID NO 42
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 42
ccaggaaacg cacatgccca ca                                              22

<210> SEQ ID NO 43
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 43
gccaagtcgt agcatttggg cc                                              22

<210> SEQ ID NO 44
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 44
agaacgtttc ccactaaaaa ga                                              22

<210> SEQ ID NO 45
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 45
aacttcttcg aacccttta tt                                               22

<210> SEQ ID NO 46
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 46
cactccctga cgactttgtg ct                                              22

<210> SEQ ID NO 47
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 47
ggtaactgaa ccgcttattt ct                                              22

<210> SEQ ID NO 48
<211> LENGTH: 22
<212> TYPE: DNA
<213> ORGANISM: Artificial Sequence
<220> FEATURE:

<223> OTHER INFORMATION: Synthetic Oligonucleotide

<400> SEQUENCE: 48
gaggaatgag cggggaggtt gg                                              22

<210> SEQ ID NO 49
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 49
aggttgtgtc ttgcgcatgg tt                                              22

<210> SEQ ID NO 50
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 50
attagatgaa cgtaaaaatg tt                                              22

<210> SEQ ID NO 51
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 51
gacatgcgct atccaccacg tagc                                            24

<210> SEQ ID NO 52
<211> LENGTH: 1006
<212> TYPE: DNA
<213> ORGANISM: Artificial Sequence
<220> FEATURE:
<223> OTHER INFORMATION: Synthetic Oligonucleotide

<400> SEQUENCE: 52
gccagtttca gttggaggag aggccacatc cactttgctg taggcctctg gttagaagca      60
tgcatggctg gctgctcctg gtctgggtcc aggggctgat acaggctgcc ttcctcgcta     120
caggagccac agcaggcacg atagatacaa agaggaacat ctctgcagag gaaggtggct     180
ctgtcatctt acagtgtcac ttctcctctg acacagctga agtgacccaa gtcgactgga     240
agcagcagga ccagcttctg gccatttata gtgttgacct ggggtggcat gtcgcttcag     300
tcttcagtga tcgggtggtc ccaggcccca gcctaggcct caccttccag tctctgacaa     360
tgaatgacac gggagagtac ttctgtacct atcatacgta tcctggtggg atttacaagg     420
ggagaatatt cctgaaggtc caagaaagct cagtggctca gttccagact gccccgcttg     480
gaggaaccat ggctgctgtg ctgggactca tttgcttaat ggtcacagga gtgactgtac     540
tggctagaaa gaagtctatt agaatgcatt ctatagaaag tggccttggg agaacagaag     600
cggagccaca ggaatggaac ctgaggagtc tctcatcccc tggaagccct gtccagacac     660
aaaactgcccc tgctggtccc tgtggagagc aggcagaaga tgactatgct gacccacagg     720
aatactttaa tgtcctgagc tacagaagcc tagagagctt cattgctgta tcgaagactg     780
gctaacgaca gctctctatc cctctcccta tgtctctctc tctgtctctc tctgtctctc     840

```
tctgtctctg tctctgtctc tgtctctctc tctctctctc tgtgtgtgtg    900
tgtgtgtatg tgtgtataca tcattaatgt tcattaacac taactgcata tggtggagga    960
ccaggaaata aagtttgtg ttgctaataa aattaagtgc taactt    1006

<210> SEQ ID NO 53
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 53
gctgtcgtta gccagtcttc gatac    25
```